(12) United States Patent
Wu et al.

(10) Patent No.: US 10,768,177 B2
(45) Date of Patent: Sep. 8, 2020

(54) BACTERIOPHAGE-BASED ELECTROCHEMICAL BIOSENSOR

(71) Applicant: The United States of America, as represented by the Secretary of Agriculture, Washington, DC (US)

(72) Inventors: Vivian C. Wu, Burlingame, CA (US); Irwin Quintela, El Cerrito, CA (US)

(73) Assignee: The United States of America, as represented by the Secretary of Agriculture, Washington, DC (US)

(*) Notice: Subject to any disclaimer, the term of this patent is extended or adjusted under 35 U.S.C. 154(b) by 142 days.

(21) Appl. No.: 16/115,957

(22) Filed: Aug. 29, 2018

(65) Prior Publication Data
US 2020/0072833 A1    Mar. 5, 2020

(51) Int. Cl.
*G01N 27/327*    (2006.01)
*G01N 33/569*    (2006.01)
*G01N 33/542*    (2006.01)

(52) U.S. Cl.
CPC ... *G01N 33/56911* (2013.01); *G01N 27/3275* (2013.01); *G01N 33/542* (2013.01); *G01N 27/327* (2013.01)

(58) Field of Classification Search
CPC ............... G01N 27/327–3272; G01N 27/3275
See application file for complete search history.

(56) References Cited

U.S. PATENT DOCUMENTS

| 2005/0003346 A1 | 1/2005 | Voorhees et al. |
| 2007/0054292 A1 | 3/2007 | Goodridge |
| 2012/0018313 A1* | 1/2012 | Guigui ............. B01D 61/145 205/777.5 |
| 2016/0061830 A1 | 3/2016 | Elias et al. |

FOREIGN PATENT DOCUMENTS

| WO | 2006105504 A1 | 10/2006 |
| WO | 2008064241 A1 | 5/2008 |

OTHER PUBLICATIONS

Köhler et al., "Colour Chart—Establishing the causes of colouring in iron oxide pigments," European Coatings Journal, Jan. 2014, pp. 24-28 (Year: 2014).*
Switaj et al., "Diagnosis and Management of Foodborne Illness," American Family Physician, vol. 92, No. 5, Sep. 1, 2015 (Year: 2015).*
WIPO Search Report dated Nov. 29, 2019.

(Continued)

*Primary Examiner* — Alexander S Noguerola
(74) *Attorney, Agent, or Firm* — John Fado; Ariel Atkinson

(57) ABSTRACT

A biosensor for detecting bacteria may use bacteriophages in a sandwich-assay system. The biosensor may include a capture element and a detection element. The capture element may include a substrate and a bacteriophage. The detection element may include a bacteriophage and a signal amplification element. The biosensor may be utilized such that the target bacterium is sandwiched between the capture element and the detection element, and a quantifiable signal may be generated to measure the amount of bacteria in a sample. The biosensor of the present invention utilizes direct sensing to detect the bacteria in the sample as opposed to indirect sensing methods.

21 Claims, 11 Drawing Sheets

(56) References Cited

OTHER PUBLICATIONS

Jurczak-Kurek, Agata et al., "Biodiversity of bacteriophages: morphological and biological properties of a large group of phages isolated from urban sewage," Scientific Reports, (2016), pp. 1-17.
Kropinski, Andrew M. et al, "Enumeration of Bacteriophages by Double Agar Overlay Plaque Assay," Bacteriophages: Methods and Protocols, vol. 1: Isolation, Characterization, and Interactions, Human Press, (2009), 501:69-76.
Niu, Yan D. et al., "Genomic, Proteomic and Physiological Characterization of a T5-like Bacteriophage for Control of Shiga Toxin-Producing *Escherichia coli* O157:H7," PLOS ONE, (2012), 7(4):1-11.
Shahrbabak, Salehe S. et al., "Isolation, characterization and complete genome sequence of Phaxl: a phage of *Escherichia coli* O157 :H7," Microbiology, (2013), 159:1629-1638.
Shrivastava, Alankar et al., Methods for the determination of limit of detection and limit of quantitation of the analytical methods Abstract, Chron Young Sci, (2011), 2(1):21-25.
Singh, Amit et al., "Bacteriophage based probes for pathogen detection," Analyst, (2012), 137:3405-3421.
Singh, Amit et al., "Recent Advances in Bacteriophage Based Biosensors for Food-Borne Pathogen Detection," Sensors, (2013), 13:1763-1786.
Tolba, Mona et al., "A bacteriophage endolysin-based electrochemical impedance biosensor for the rapid detection of Listeria cells," Analyst, (2012), 137:5749-5756.

\* cited by examiner

BACTERIOPHAGE-BASED ELECTROCHEMICAL BIOSENSOR

BACKGROUND

Bacteriophages have become a promising approach as biocontrol agents due to the continuous unraveling of new information about its biology, host specificity, impacts on normal microflora and mammalian cells as well as ease of propagation (Shahrbabak, et al. Isolation, characterization and complete genome sequence of PhaxI: a phage of *Escherichia coli* O157:H7, *Micro.* 159, 1629-1638, 2013). Advanced technologies can ensure absence of virulence or antibiotic resistance genes increasing its efficacy and level of safety in phage therapy. In addition, bacteriophages that are highly-infective over a range of target groups and possess lytic life cycle that prevents recombination of its DNA with bacterial chromosome are key characteristics of excellent agents for biocontrol use. Because bacteriophages are bacterial predators, they can provide natural and non-antibiotic options that can reduce the incidence of foodborne pathogen contamination from bacteria, such as, for example, Shiga-toxin producing *Escherichia coli* (STEC) serogroups.

Specific and rapid detection of foodborne pathogens in the food system is significant for containment and prevention of human, animal and plant diseases (Singh, et al. Bacteriophage based probes for pathogen detection, *Analyst,* 137, 3405 2012). Biosensors overcome the limitations of traditional foodborne pathogen detection such as tedious and time consuming by providing reliable, specific and highly sensitive platforms with shorter turnaround time. More importantly, bio sensors circumvent the limitations of the traditional laboratory microbial screening by its hand-held features and portability for on-site rapid analysis and detection of significant groups of foodborne pathogens and toxins. Bacteriophages possess excellent host selectivity attributes and have been used as biorecognition elements for pathogen detection (Singh, et al. Recent Advances in Bacteriophage Based Biosensors for Food-Borne Pathogen Detection, *Sensors,* 13, 1763-1786, 2013).

The use of antibodies as recognition elements is very common in diagnostics and foodborne pathogen biosensing applications due to their availability and high affinity. Monoclonal and polyclonal antibodies provide selectivity and specificity when incorporated as receptors. However, the major drawbacks of antibodies that are constantly met by end-users include high costs of production, instability and that they are highly prone to contamination and degradation rendering them very impractical and unreliable recognition elements. In addition, cross-reactivity towards other strains or species and interference are innate to polyclonal antibodies.

Bacteriophages that exist in nature and are inexpensive to propagate may be alternatives to antibodies as biological recognition receptors as they are highly-specific to their host bacteria and very stable, which allows easy handling and storage. However, once a bacteriophage binds to and/or infects a target bacterium, the bacterium is time-limited in that it will be killed by the phage, and thus is difficult to detect directly.

All of the references cited herein, including U.S. Patents and U.S. Patent Application Publications, are incorporated by reference in their entirety.

Mention of trade names or commercial products in this publication is solely for the purpose of providing specific information and does not imply recommendation or endorsement by the U.S. Department of Agriculture.

SUMMARY

A biosensor for detecting bacteria may use bacteriophages in a sandwich-assay system. The bio sensor may include a capture element and a detection element. The capture element may include a substrate and a bacteriophage. The detection element may include a bacteriophage and a signal amplification element. The biosensor may be utilized such that the target bacterium is sandwiched between the capture element and the detection element, and a quantifiable signal may be generated to measure the amount of bacteria in a sample. The biosensor of the present invention utilizes direct sensing to detect the bacteria in the sample as opposed to indirect sensing methods.

According to at least one embodiment of the invention, a bio sensor may include a capture element, itself including a substrate, a surface of the substrate being functionalized with at least one capturing bacteriophage; and a detection element, itself including a at least one detection bacteriophage conjugated to a signal amplification element, and the capturing bacteriophage and the detection bacteriophage may be configured to bind to the same strain or species of a target bacterium.

According to a further embodiment, the capturing bacteriophage and the detection bacteriophage may both be functionalized with conjugating elements.

According to a further embodiment, the capture element may also include a linking molecule which serves to affix the capturing bacteriophage to the substrate.

According to a further embodiment, the signal amplification element may include a particle, the particle being one of a metal particle, a metal oxide particle, or a semiconductor particle.

According to a further embodiment, the signal amplification element may include a catalyst.

According to a further embodiment, the bio sensor may also include a signal detection device communicatively connected to the capture element. The biosensor may also optionally include a control device.

According to a further embodiment, the biosensor is operable using direct sensing of the target bacterium.

According to another embodiment of the invention, a kit for the detection of a target bacterium may include a capture element, itself including a substrate, a surface of the substrate being functionalized with at least one capturing bacteriophage; and a detection element, itself including a at least one detection bacteriophage conjugated to a signal amplification element, and the capturing bacteriophage and the detection bacteriophage may be configured to bind to the same strain or species of a target bacterium.

According to a further embodiment, the kit may also include a signal detection device communicatively connected to the capture element.

According to a further embodiment, the signal amplification element may include a particle and a catalyst, the particle being one of a metal particle, a metal oxide particle, or a semiconductor particle.

According to a further embodiment, the kit is operable using direct sensing of the target bacterium.

According to another embodiment of the invention, a method for detecting a target bacterium in a sample may include (1) performing a capture incubation step, the step comprising introducing a capture element to the sample and incubating for a pre-determined capture time; (2) following the capture incubation step, performing a sandwich incubation step, the step comprising introducing a detection element to the capture element and incubating for a pre-determined sandwich time; and (3) following the sandwich incubation step, generating a signal to detect the target bacterium, wherein the capture element includes a substrate and a capturing bacteriophage functionalized thereon, and the detection element includes a detection bacteriophage conjugated to a signal amplification element.

According to a further embodiment, the pre-determined capture time may be between 8-16 minutes.

According to a further embodiment, the pre-determined sandwich time may be between 6-14 minutes.

According to a further embodiment, the method may also include introducing an activator.

According to a further embodiment, the sandwich incubation step may generate a sandwich complex, the sandwich complex having the target bacterium disposed between the capture element and the detection element.

According to a further embodiment, the method may also include introducing a mediator.

According to another embodiment of the invention, a kit for making a biosensor may include a substrate and a signal amplification element, where both the substrate and the signal amplification element are functionalized so as to be ready to conjugate with a bacteriophage. The kit for making a biosensor may optionally additionally include instructions as to how to amend the components of the kit with a bacteriophage of the user's choice so as to create a biosensor for detecting a bacterium in a sample.

BRIEF DESCRIPTION OF THE FIGURES

Advantages of embodiments of the present invention will be apparent from the following detailed description of the exemplary embodiments. The following detailed description should be considered in conjunction with the accompanying figures in which.

Exemplary

Exemplary

Exemplary

Exemplary

Exemplary

Exemplary

Exemplary

Exemplary

Exemplary

Exemplary

Exemplary

Exemplary

DETAILED DESCRIPTION

Figure 1:
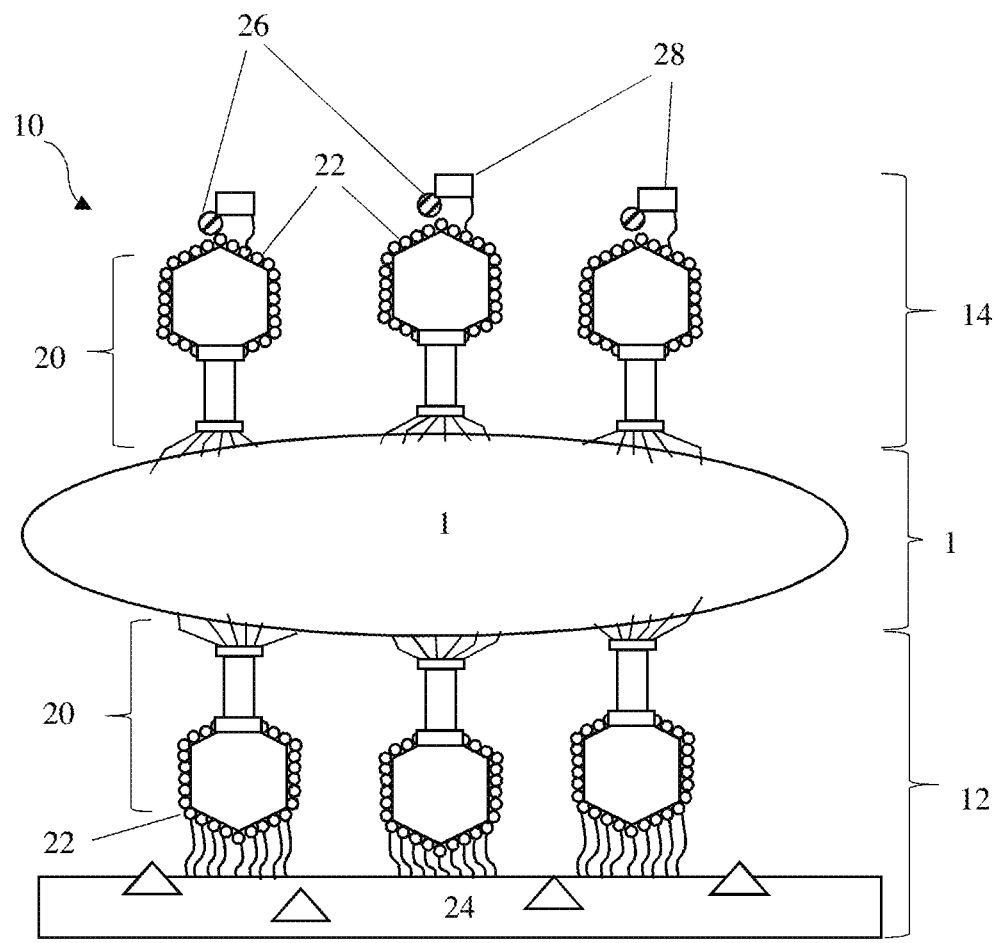
FIG. 1 shows a schematic of the bio sensor in use, including the capture element, the detection element, and a target bacterium.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

The term "biosensor" refers to an analytical device or system which integrates biologically sensitive materials as recognition elements and can generate a quantifiable signal proportional to the concentration of a target. The target may be a molecule, organism, or other chemical or biological entity. The signal may be generated by any conventional means, such as electroanalytical or electrochemical techniques and methods.

The term "bacteriophage" or "phage" refers to a virus which binds to and infects a bacterium. Individual strains of bacteriophages are generally known in the art to be specific to certain species or strains of bacteria.

Unless defined otherwise, all technical and scientific terms used herein have the same meaning as commonly understood by one of ordinary skill in the art to which the invention belongs. As used herein, the term "about" refers to a quantity, level, value, or amount that varies by as much as 30%, preferably by as much as 20%, and more preferably by as much as 10% to a reference quantity, level, value, or amount. Although any methods and materials similar or equivalent to those described herein can be used in the practice or testing of the present invention, the preferred methods and materials are now described.

The amounts, percentages, and ranges disclosed herein are not meant to be limiting, and increments between the recited amounts, percentages, and ranges are specifically envisioned as part of the invention.

"Optional" or "optionally" means that the subsequently described event or circumstance may or may not occur, and that the description includes instances in which said event or circumstance occurs and instances where it does not. For example, the phrase "optionally comprising X" means that the composition may or may not contain X, and that this description includes compositions that contain and do not contain X.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein.

According to at least one exemplary embodiment, a biosensor may utilize bacteriophages to directly detect a target bacterium. The biosensor may utilize a sandwich-type recognition approach and an electroanalytical method to generate a readable signal. An exemplary schematic of a biosensor according to the present invention is shown in FIG. 1. A target bacterium 1 may be detected by using a biosensor 10, which includes a capture element 12 and a detection element 14. The capture element 12 and the detection element 14 may both utilize a bacteriophage 20 which may be functionalized with a conjugating element 22. The conjugating element may be, for example, biotin. The bacteriophages 20 in the capture element 12 may be affixed to a substrate 24 by any conventional means, for example through the conjugating element 22. The detection element 14 may additionally have signal amplification elements, including one or more metal particles 26 and an oxidation catalyst 28.

The biosensor may be communicatively connected to a signal detection device, such as an electrometric device, and a control device, such as a type of computer. The control device may receive a signal from the signal detection device and convert it into readable data for an end user.

The target bacterium for the biosensor may be any bacterium. The bacteriophage used in a biosensor according to the present invention can be determined by known means once a target bacterium is chosen; methods for determining whether a particular phage is specific and/or sensitive to a particular target bacterium are well-known in the art, and an exemplary method is also described below in the Examples. Exemplary bacteria which may be targets for a biosensor according to the present invention include, but are not limited to, *E. coli, Listeria monocytogenes, Campylobacter* spp., and *Staphylococcus* spp.

The bacteriophages used in a biosensor according to the present invention may be conjugated for use in the biosensor by using a conjugating element. In particular, conjugation may be accomplished by functionalizing the phage with a conjugating element, such as biotin, histadine-tagged nitrilo acetic acid, dithiobis succinimidyl propionate, and other genetically engineered protein affinity ligands.

To attach the bacteriophages to a substrate for use in a capture element according to the present invention, a linking molecule or compound may be used. The linking molecule may be attached directly to the bacteriophage or to a conjugating element. Exemplary linking molecules include, but are not limited to, streptavidin, ethanolamine, and other amine-containing compounds.

The substrate used in a biosensor according to the present invention may be a solid surface on which to mount the biosensor. The substrate may also include electrically-conductive elements to assist in generation and/or detection of a signal. The substrate may be, for example, a printed electrode, a printed circuit board, a silicon- or carbon-based board, or a glass substrate with metal interdigitated electrodes. Further, the substrate may be printed, impregnated, or treated with additional elements to assist with the operation of the biosensor, as desired.

The detection element may use metal, metal oxide, or semiconductor particles and/or catalysts to assist with signal production and amplification. The metal particles may be metallic nanoparticles, such as gold nanoparticles, silver nanoparticles, or platinum nanoparticles. Metal oxide nanomaterials such as zinc oxide may also facilitate signal enhancement. The catalyst may be a catalyst to assist in a redox reaction or any other electrochemical reaction. Exemplary catalysts which may be used in the present invention include, but are not limited to, peroxidases, including horseradish peroxidase, soybean peroxidase, glucose oxidase, acetyl cholinesterase, and galactose oxidase. Alternatively, the detection element may have other signal amplification elements which can be used to create a detectable, quantifiable signal, as may be known in the art.

The biosensor according to the present invention makes use of direct sensing. Direct sensing is the sensing of an analyte, such as the target bacterium, itself without using secondary products. It is distinguished from indirect sensing, which in the case of a phage-based assay would involve the additional step of infecting the target bacterium, killing it, and then measuring an output, whether that output is an increased number of phages in the system or another chemical or biological marker which is released upon the death of the bacterium. Direct sensing uses the desired phage to detect and attach to the bacterium, but does not require the phage to kill the bacterium. According to at least one embodiment of the invention, where a sandwich-type assay approach is used, total cell death of the bacterium to where it breaks apart prior to the detection element attaching to the bacterium would be undesirable. This is in contrast to indirect sensing methods where total cell death of the bacterium to where it breaks apart is necessary.

The biosensor according to the present invention may function as follows: a target sample in solution may be introduced to the capture element, and incubated for a short time, such as between 8-16 minutes, or as desired for a particular analyte, such as about 10-14 minutes. Following an optional washing, the detection element may then be introduced to the system and incubated for a short time, such as 6-14 minutes, or as desired for a particular analyte, such as about 8-12 minutes. Following an optional washing, a mediator, such as 1,1'-ferrocenedicarboxylic acid, 2-ferrocenyl-4-nitrophenol, or potassium hexacyanoferrate and/or an activator, such as hydrogen peroxide may be added and optionally incubated with the system. A signal may then be generated, such as through electrochemical methods, to effectively analyze the sample.

According to at least one exemplary embodiment of the invention, a kit may include a capture element and a detection element, or the constituent parts thereof. A sample to be evaluated for a target bacterium may be incubated with the capture element to capture any target bacteria. The capture element, potentially now having captured target bacteria, may then be incubated with the detection element to create a capture-bacterium-detection complex. The complex may then be interrogated, such as by using electrical methods, to create a quantifiable signal communicating the amount or concentration of target bacteria in the sample.

Further embodiments and features of the present invention may be understood from the following examples.

Example 1

Isolation and Characterization of STEC-Specific Bacteriophages

Known bacteria samples were used to assess bacteriophages isolated from the environment. All bacterial strains used were part of the University of Maine-Pathogenic Microbiology Laboratory, Orono, Me. and USDA-Agricultural Research Services (ARS) Centers (Produce Safety and Microbiology Unit, Albany, Calif. and Wyndmoor, Pa.) strain collections. Representative strains of each top six STEC serogroups (O26, O45, O103, O111, O121, and O145), O157 ATTC (ATCC 43888), and non-O157 (O179) were included. Other non-STEC strains, *Salmonella Typhimurium* ATCC 14028, *S. Typhimurium* ATCC 6962 and *Listeria monocytogenes* ATCC 19115 and generic *E. coli* were used to assess host range and lytic capabilities of the environmentally isolated bacteriophages. Frozen bacterial strains in cryogenic beads (CryoSavers; Hardy Diagnostics, Santa Maria, Calif.) were initially activated then revived in Brain Heart Infusion (BHI) broth (Neogen, Lansing, Mich., USA) at 37° C. Viability of strains was confirmed using appropriate selective agar media, MacConkey Agar with Sorbitol (Neogen) for STEC strains, xylose lysine deoxycholate (XLD) agar (Neogen) for *Salmonella* spp. strains and Palcalm agar (Neogen) for *L. monocytogenes*.

Cow manure to be used for bacteriophage isolation was collected from cows located in Maine. Each fresh manure sample (approximately 300 g) was freshly picked and placed in sterile bags (Whirlpak; Fisher Scientific, Wilmington, Del.) before transporting to the laboratory in an iced container within 6 hours of collection. Since cow manure samples originated from various sources, the pH of each sample was measured and recorded prior to storage at −20° C. In addition, one trough water sample from crop-growing areas in Salinas, Calif. was also used to isolate bacteriophages from the natural environment.

Approximately 10 mL of environmental sample was mixed with modified 90 mL Tryptic Soy Broth (mTSB) containing 8 mg/L novobiocin and casamino acids (Neogen) and then mixed. Homogenized samples were centrifuged before collecting the supernatant, followed by mixing with a cocktail of seven overnight representative STEC pure culture strains (300 μL each) and $CaCl_2$ (10 mmol/L, final concentration). Mixtures were incubated overnight (37° C.). To kill all bacterial cells, chloroform (4% v/v, final concentration) was added and kept at room temperature for 30 min. Medium speed centrifugation was conducted for 15 min to collect the supernatant where potential bacteriophages were suspended.

To determine the specific susceptible STEC host strain, a 10,000-fold diluted supernatant (with potential bacteriophages) was spotted (10 μL) on various Tryptic Soy Agar (TSA) (Neogen) plates with overnight lawn of individual STEC strains. Formation of spots after an overnight incubation at 37° C. confirmed bacteriophage specificity and STEC host susceptibility. Spots were picked and mixed with the corresponding STEC host for enrichment in Tryptic Soy Broth (TSB) with $CaCl_2$ (10 mmol/L, final concentration) under the same incubation conditions as used previously.

Bacteriophage isolates were then subjected to a soft agar overlay technique as previously described by Kropinski, et al. (Enumeration of Bacteriophages by Double Agar Overlay Plaque Assay in *Bacteriophages: Methods and Protocols, Vol* 1, Humana Press 2009) in three cycles to purify individual bacteriophages. In brief, a bacteriophage suspension was mixed with its host bacterium and distributed evenly to solidify on a bottom agar plate (TSA). After an overnight incubation at 37° C., a zone of clearing that showed in the overlay was sliced, picked and resuspended in phosphate-buffered saline (PBS). Enriched bacteriophage samples were then were filtered using a 0.2 μm membrane (Millipore, Billerica, Mass.) before performing plaque assay on TSA for titer level (PFU/mL) evaluation. All enriched bacteriophages were stored in TSB at 4° C. until further use.

Bacteriophages that formed clear plaques during the spot assay were re-tested against non-STEC strains to determine specificity, host range, host susceptibility and lytic capability. In brief, non-STEC overnight cultures were mixed with molten TSA and incubated over night at 37° C. to create a lawn of bacteria. High titer bacteriophages stock solution was spotted on the agar and also incubated overnight at 37° C. Representative STEC bacteriophages were also tested for multiplicity of infection (MOI) (Niu, et al. Genomic, Proteomic and Physiological Characterization of a T5-like Bacteriophage for Control of Shiga Toxin-Producing *Escherichia coli* O157:H7, PLoS One, 7:4, 2012).

Conventional PCR was also performed to determine the presence of STEC virulence genes, stx1 and stx2. In brief, bacteriophage genomic DNA was extracted from purified bacteriophages using Phage DNA Isolation Kit (Norgen Biotek Corp, Ontario, Canada) following manufacturer's directions.

In total, 21 bacteriophages were isolated, all of which lysed representative bacterial strains of various STEC serogroups and displayed no biological activities (i.e. no cell lysis and plaques formation) against non-STEC strains (*S. Typhimurium*, *L. monocytogenes* and generic *E. coli*).

Plaque morphologies were very similar among the isolates; most of it formed clear plaques which was common for virulent or lytic bacteriophages. The average diameter was in the range of 1-1.5 mm in TSA plates. In addition, STEC bacteriophages showed similar infective patterns against STEC strains. Relative to host susceptibility, MOI value was used as a parameter to classify host-bacteriophage interaction and infection. It is the lowest ratio of bacteriophage and STEC bacteria that resulted to complete lysis or lowest absorbance (least turbid) of an overnight STEC culture during 5 h of incubation with serially diluted bacteriophages. STEC O26 and O45 representative strains were highly susceptible bacterial hosts based on MOI, in the 0.5-0.875 range. Molecular characterization showed selected STEC bacteriophages were devoid of stx1 or stx2 gene; only one bacteriophage isolate specific to STEC O26 generated an amplicon.

Further, for morphological characterization of isolated bacteriophages, transmission electron microscopy (TEM) was used. Purified bacteriophage stock solution was ultra-centrifuged, and samples were washed in PBS buffer before dropping onto carbon-coated films on copper grids. TEM samples on grids were negatively stained using 1.5% uranyl acetate (pH 4-4.5) and air-dried before viewing under a TEM (Tecnai G2 F20; FEI, USA) at 200 kV.

Figure 2A:
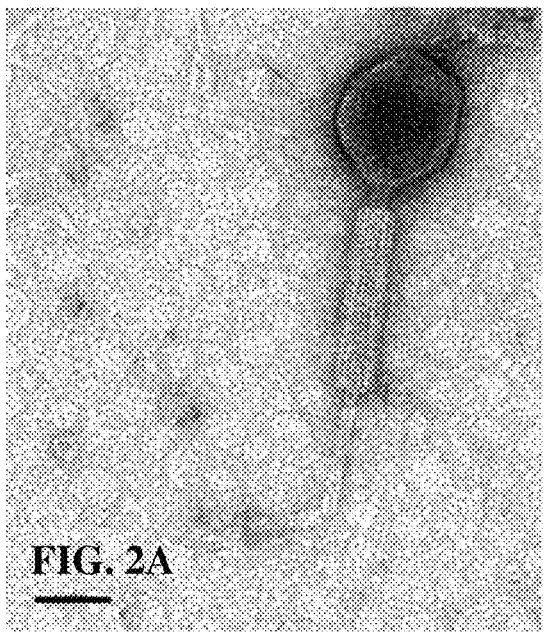
FIG. 2 shows TEM images of various STEC-specific bacteriophage isolates, including a STEC O157:H7 bacteriophage (A), a STEC O121:H19 SJ18 bacteriophage (B), a STEC 121:H19 96-1585 bacteriophage (C), and a STEC O103 bacteriophage (D). The scale bars are 50 nm.
Figure 2B:
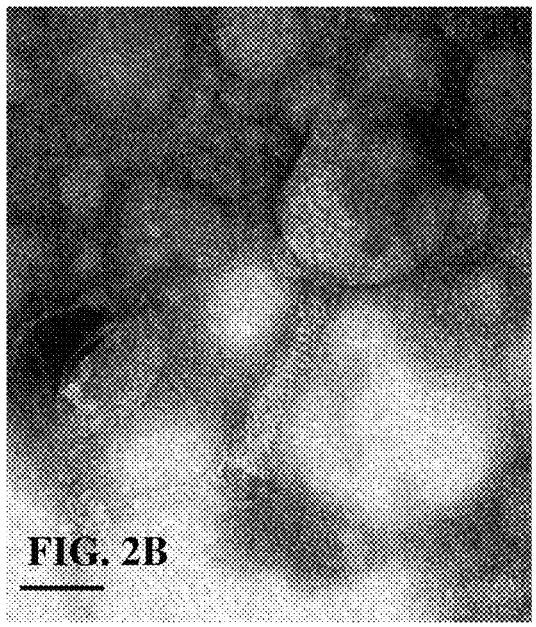
Figure 2C:
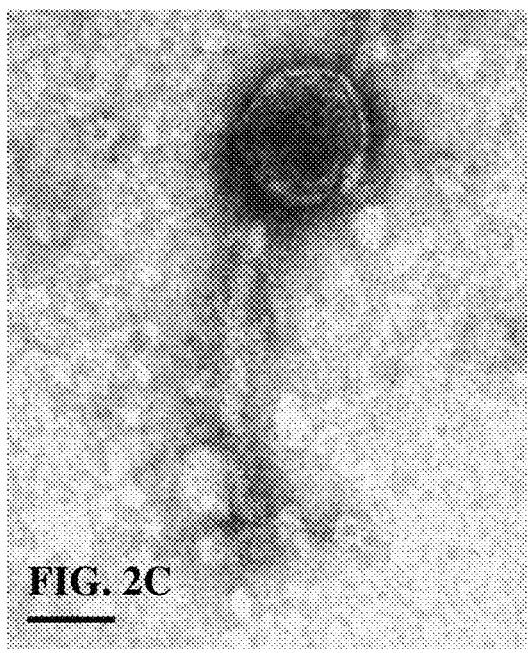
Figure 2D:
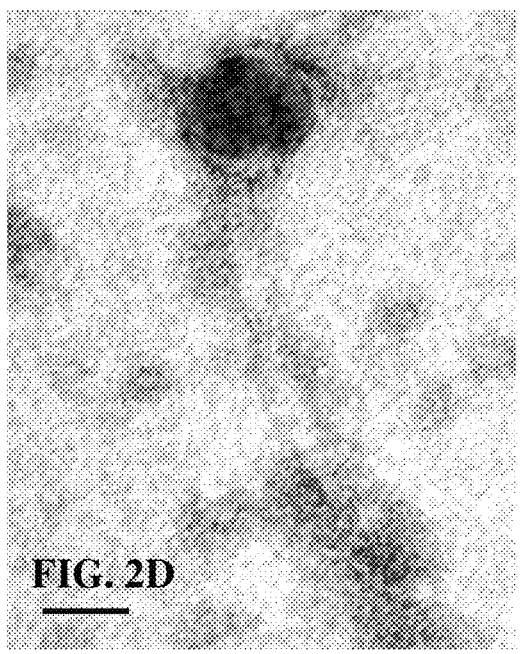
Figure 3A:
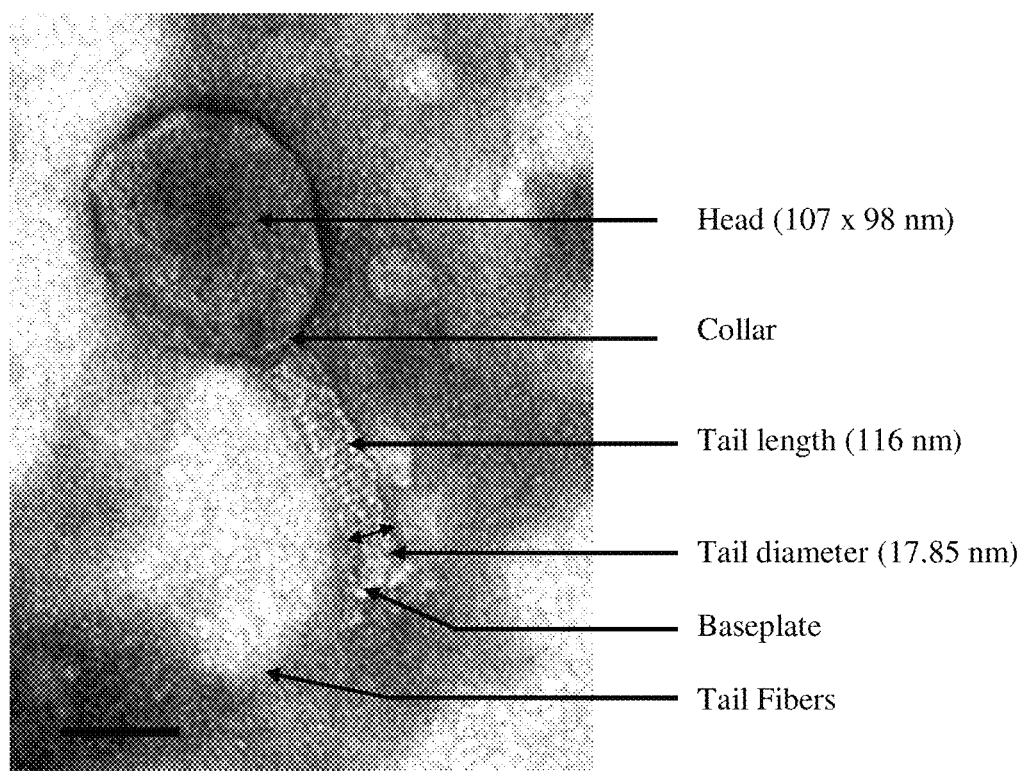
FIG. 3A shows the ultrastructures of a STEC O121:H19 SJ18 bacteriophage having a complete icosahedral head and a long tail with appending tail fibers radiating from the base plate, suggesting that it belongs to Myoviridae. The scale bar is 50 nm.
Figure 3B:
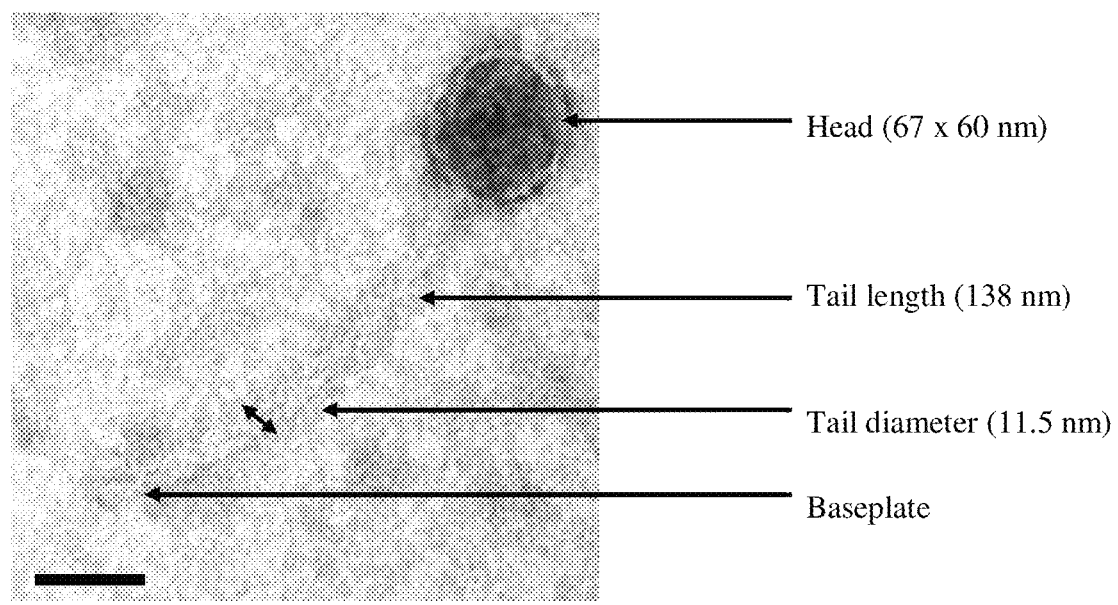
FIG. 3B shows the ultrastructures of a STEC O103 bacteriophage having a smaller icosahedral head and baseplate which is typical STEC bacteriophage and suggesting that it belongs to Siphoviridae. The scale bar is 50 nm.
Figure 3C:
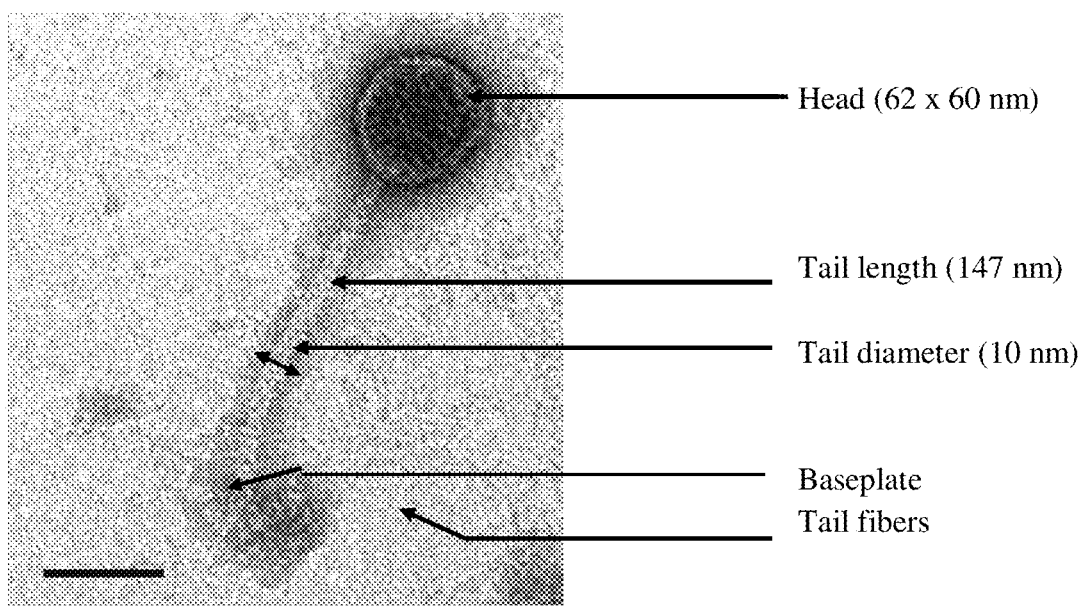
FIG. 3C shows the ultrastructures of a STEC O179 bacteriophage under family Siphoviridae. The scale bar is 50 nm.

All of the bacteriophages studied belonged to tailed-bacteriophage order Caudovirales based on the established parameters in published literatures. Published bacteriophage morphological dimensions have allowed grouping of the isolates into three families (Siphovidirae, Myoviridae and Podoviridae) under the order Caudovirales (Jurczak-Kurek, et al. Biodiversity of bacteriophages: morphological and biological properties of a large group of phages isolated from urban sewage, *Sci. Reports*, 6:34338, 2016). FIG. 2 shows four bacteriophage isolates specific to STEC O157: H7, O121 and O103. A prominent morphological feature of the STEC O157 bacteriophage was its contractile sheathed-tail that extended and covered more than half of its tail length (FIG. 2A). Other features such as collar, base plate and tail fibers were also observed in some isolates. The tail fibers that radiated from the baseplate of STEC O121:H19 SJ18 bacteriophage can be clearly seen in FIG. 2B. FIGS. 3A-3C show the ultrastructures of bacteriophages O121, O103, and O179, respectively, with dimensions. The diameter of the icosahedral head (width perpendicular to the tail), head length (along the tail axis), tail length as well as tail diameter were all measured.

Based on the morphologies observed, the isolated bacteriophages were from families Myoviridae and Siphoviridae. For bacteriophages that possess tails longer than 40 nm, which was all of the phages isolated here, they can be classified under either Myoviridae or Siphoviridae based on tail diameter, specifically >16 nm (Myoviridae) or <16 nm (Siphovidirae).

Example 2

Bacteriophage-Based Biosensor

Bacteriophages as described in Example 1 were chemically modified to assist with the creation of the biosensor. The concentration (μg/mL) of high-titer bacteriophage stocks (>9 log PFU/mL) was determined using Pierce™ BCA Protein Assay Kit (Fisher Scientific, Wilmington, Del.) following manufacturer's instructions. In brief, a standard concentration curve of known protein diluted bovine serum albumin (BSA), supplied in the kit was initially created as the basis for measuring the concentration of bacteriophage sample stock solution. A microplate reader was set at 562 nm to generate absorbance data to plot the curve.

After measuring the concentration (μg/mL) of purified bacteriophage stocks in 1×PBS, bacteriophages stocks were then biotinylated with increasing concentrations of sulfosuccinimidobiotin (EZ-Link™ Sulfo-NHS-Biotin, Fisher) ranging from 1-20 mM. Bacteriophage-sulfosuccinimidobiotin sample mixtures were incubated at 4° C. overnight and dialyzed against 1×PBS to remove excess unbound biotin following manufacturer's protocol. Incorporated biotin was measured colorimetrically (at 500 nm) using HABA (4'-hydroxyazobenzene-2-carboxylic acid, Fisher) reagent following the manufacturer's protocol. In addition, to determine the optimum concentration of biotin, the maximum viability (titer level, PFU/ml) retention of bacteriophages was investigated by conducting plaque assays at pre- and post-biotinylation stages. Table 1 shows the results of the biotinylation of the bacteriophages. For these results, O179 phages were used.

TABLE 1

Biotinylation of O179 Bacteriphages (initial PFU/mL: 10.85)

| Biotin (mM) | Bound biotin/ mole protein | Measured PFU/mL of modified phages | Viability of modified phages |
|---|---|---|---|
| 0 | 0 | 10.85 | 100% |
| 1 | 49.37 | 10.11 | 93.18% |
| 5 | 95.71 | 10.36 | 95.48% |
| 10 | 98.15 | 10.25 | 94.47% |
| 15 | 103.02 | 10.41 | 95.94% |
| 20 | 121.93 | 10.36 | 95.48% |

To monitor and investigate the effects of biotin on the morphology, biotinylated bacteriophages were coupled with streptavidin-coated nanocrystals (Qdots, Fisher) and viewed under the transmission electron microscope (TEM). No nanocrystals were observed to have bound to samples in the control (0 mM) or 1 mM groups. On the samples in the 5, 10, and 15 mM groups, bound crystals were easily observed with no major morphological changes on the bacteriophages. In the 20 mM group, the bacteriophage capsid appeared to be thickened, and visible heavy mass structures had accumulated along its periphery and toward the center (TEM images not shown).

All modified bacteriophages were initially suspended in 1×PBS and stored at 4° C. prior to their use. No activation was needed for all the modified bacteriophages (specific to STEC O26:H11, STEC O157:H7 and STEC O179) that were used to target host bacteria in this Example.

Figure 4:
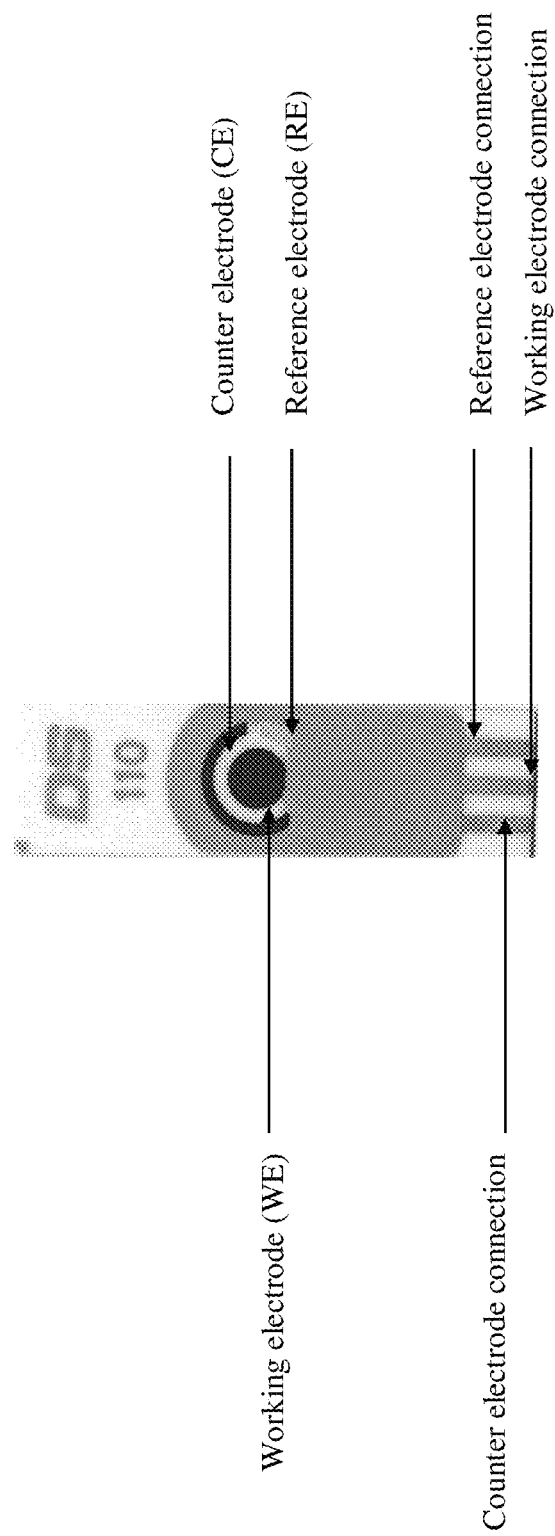
FIG. 4 shows a screen-printed carbon electrode (SPCE) including the working electrode, the counter electrode, and the reference electrode.
Figure 5A:
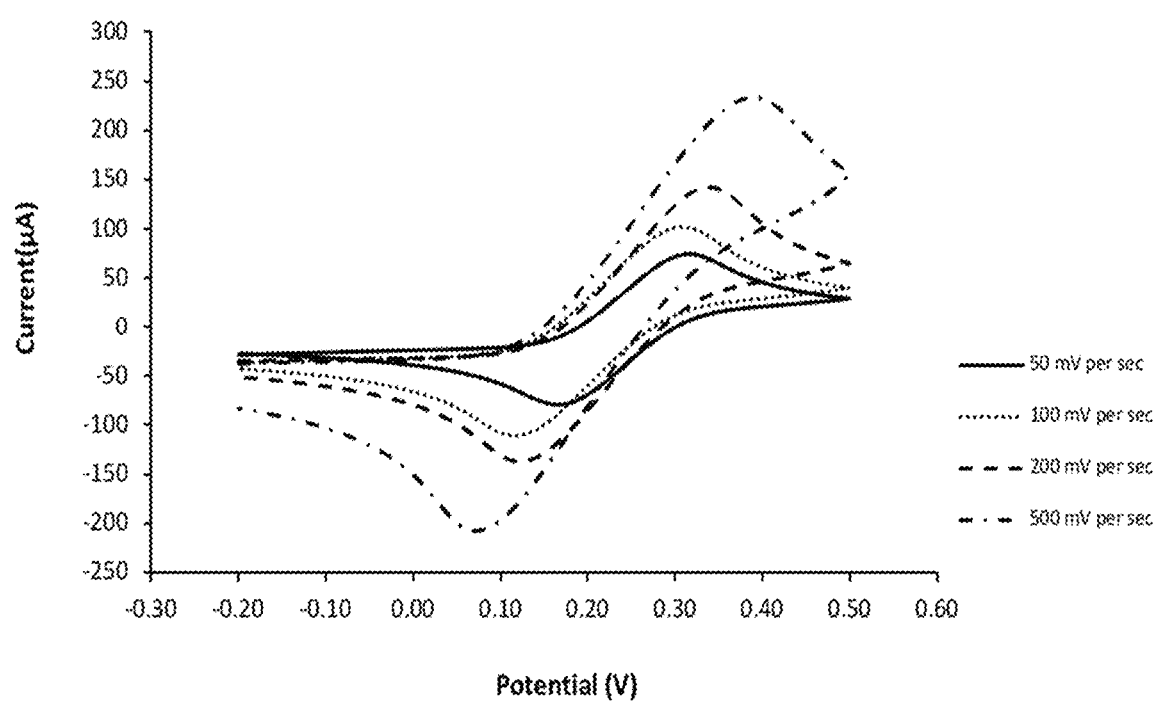
FIG. 5A shows cyclic voltammetry conducted with an unmodified electrode and 0.5 mM $K_3[Fe(CN)_6]$ in 0.1M sulfuric acid at increasing scan rates under the same potential step (−0.5 V to +0.5 V vs counter/reference electrode).
Figure 5B:
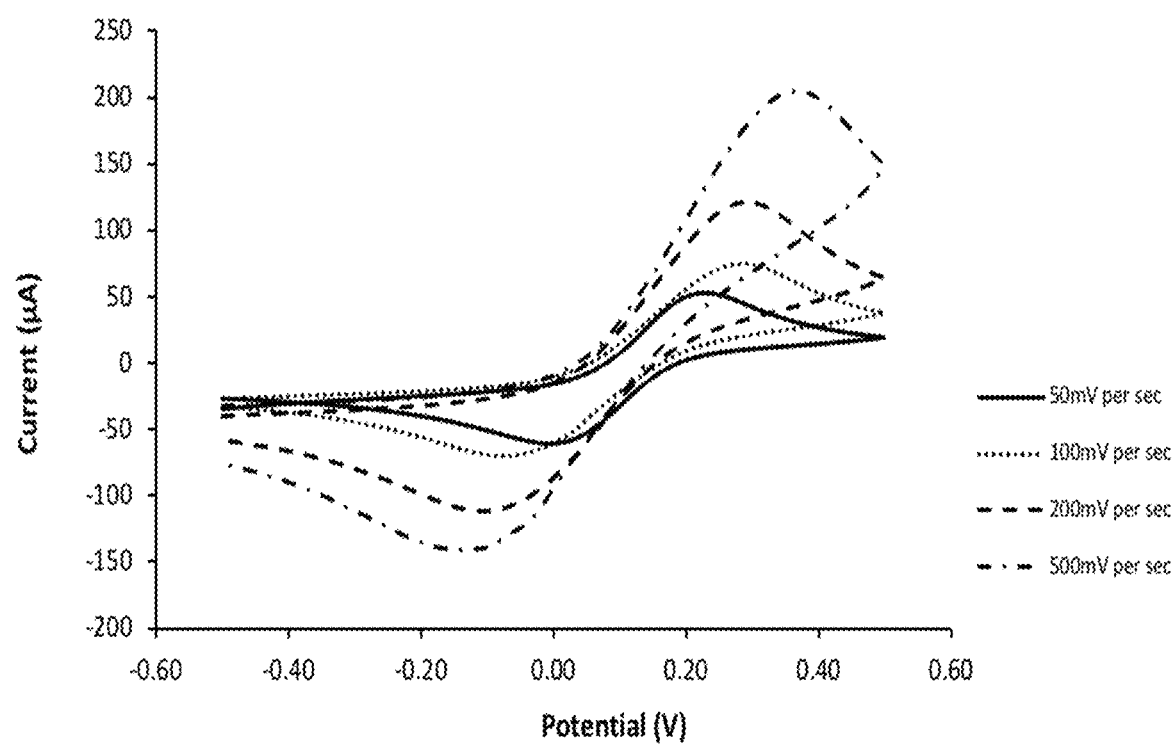
FIG. 5B shows cyclic voltammetry conducted with an unmodified electrode and 0.5 mM $K_3[Fe(CN)_6]$ in 1×PBS at increasing scan rates under the same potential step (−0.5 V to +0.5 V vs counter/reference electrode).

A capture element for the biosensor was built on a screen-printed carbon electrode (SPCE). The SPCEs used here were purchased from DropSens (Asturias, Spain). These planar SPCEs had a circular carbon working electrode (WE) (4 mm diameter), a carbon counter electrode (CE), and a silver reference electrode (RE) (FIG. 4). Electrochemical measurements were conducted with a PalmSens3 Electrochemical Portable Apparatus—Potentiostat/Galvanostat/Impedance Analyser (PalmSens Instrument BV, Houten, The Netherlands) which was wirelessly connected via Bluetooth™ and controlled by an Android™ device.

Unmodified SPCEs were electrochemically characterized by recording cyclic voltammograms (CV) of 0.5 mM $K_3[Fe(CN)_6]$ in two separate supporting electrolytes, acid (0.1 M $H_2SO_4$) and salt (1×PBS) at increasing scan rates (50 mV/sec, 100 mV/sec, 200 mV/sec and 500 mV/sec) under the same potential step (−500 mV to +500 mV vs counter/reference electrode). SPCEs were previously rinsed with sterile distilled water and further cleaned with ethyl alcohol before air drying. Resulting cyclic voltammograms are shown in FIGS. 4A (sulfuric acid) and 4B (1×PBS). Oxidation and reduction peak potentials during the scans were generated to identify the peak separation ($\Delta E_p = E_p^c - E_p^a$, where $E_p^c$ is the cathodic peak and $E_p^a$ is anodic peak) of the redox system for quality evaluation of the surface of the SPCEs. Lower $\Delta E_p$ or peak separation values tends to correlate with better quality of electrode surface as well as the optimum parameters used such as the scan rate. Following this testing, all succeeding electrochemical tests were conducted using 1×PBS at 100 mV/s scan rate (which had a $\Delta E_p$ of 150.3) unless otherwise indicated. However, an optimum scan rate and electrolyte may be adjusted as desired by a potential user, and as affected by the materials chosen.

To create the capture element, elements were added to the SPCE in a step-wise fashion. First, to introduce carboxyl (—COOH) onto the clean WE surface, carboxymethyl (CMD) dextran sodium salt (Sigma-Aldrich) was added (20 μL, 50 mg/mL) and incubated for 3 hours with shaking at room temperature. Then, an equal volume of N-(3-dimethylaminopropyl)-N'-ethylcarbodiimide hydrochloride (EDC)

(0.4M, Sigma-Aldrich) and sulfo-N-hydroxysulfosuccinimide (NHS) (0.1M, Thermofisher Scientific) were added to activate the —COOH. After the activation, streptavidin (20 μL, 50 μg/mL, Thermofisher Scientific) which carries an amine, was transferred and incubated for 40 mins to allow carboxyl-to-amine crosslinking. Excess liquid was removed and the modified SPCEs were kept in humidified containers before adding biotinylated bacteriophages (20 μL, >8 log PFU/mL), for overnight incubation at 4° C. Biofunctionalized SPCEs with immobilized biotinylated bacteriophages were blocked with 30% casein (20 μL) overnight at 4° C. before washing them twice with 20×TBS (TBS-T20) (Thermofisher Scientific) and once with 0.5×PBS. All biofunctionalized SPCEs/capture elements were stored at 4° C. until further use. The bioactivity of two-day old capture elements of biomodified-SPCE was evaluated using agar diffusion test with a lawn of overnight host bacterium.

Successfully biomodified SPCEs (capture element) were characterized by comparing their cyclic voltammograms with the unmodified form of SPCE. Individual reagents were serially added to the working electrode based on previously determined optimized conditions. In brief, SPCE was initially activated with CMD-Dextran, then EDC-NHS, and streptavidin were added prior to the immobilization of STEC O179-specific biotinylated bacteriophages. A blocking reagent (30% casein) and a mediator (1,1'-ferrocenedicarboxylic acid, FeDC) were also applied before conducting CV testing at 100 mV/sec with 0.5 mM $K_3[Fe(CN)_6]$ in 1×PBS as the electrochemical probe. The results of the CV testing are shown in Table 2 below:

TABLE 2

Electrochemical testing of variously modified SPCEs

| Modified SPCE | $\Delta E_p$ (mV) |
|---|---|
| CMD-dextran modified | 160.481 |
| EDC-NHS modified | 201.023 |
| Streptavidin modified | 216.228 |
| Bacteriophage modified | 236.499 |
| FeDC modified | 216.227 |
| AuNP modified | 207.781 |
| BSA modified | 216.227 |
| Casein modified | 206.091 |
| Protein free modified | 206.091 |
| PEG | 195.956 |

Figure 6:
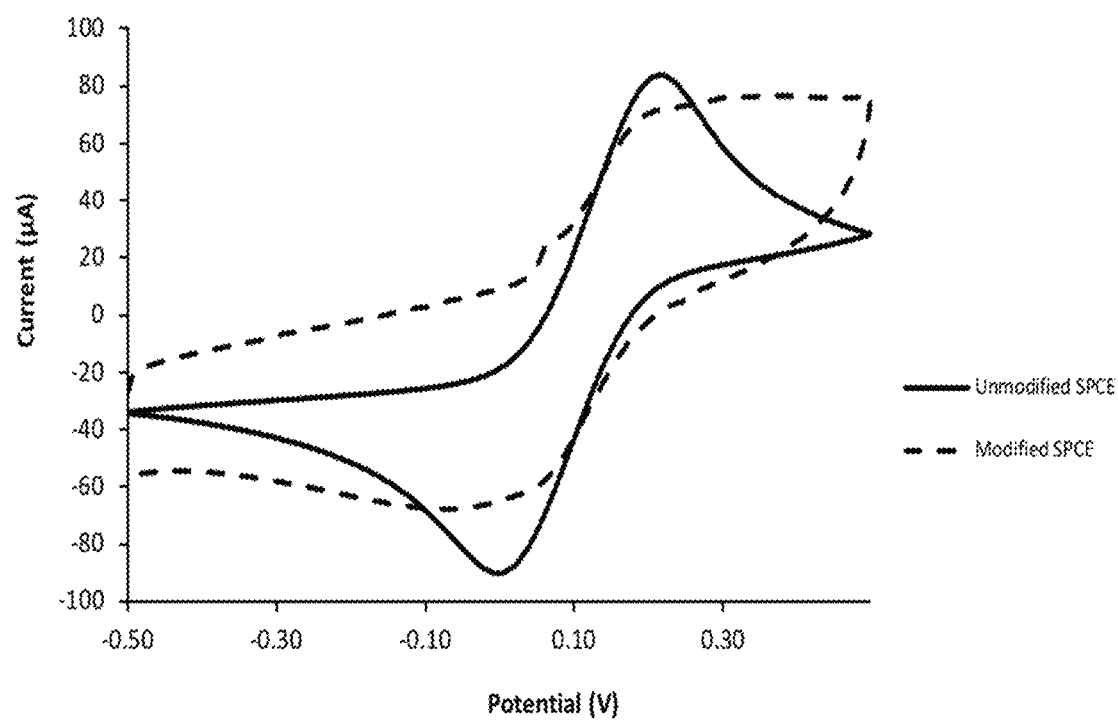
FIG. 6 shows cyclic voltammetry conducted with an unmodified SPCE and a capture element according to the present invention.

To illustrate the difference between the unmodified SPCE and the capture element, FIG. 6 shows a cyclic voltammogram of those. The capture element here has been blocked by casein and a mediator (FeDC) has been applied. Results showed the difference between $\Delta E_p$ of the unmodified and biofunctionalized SPCE which had 170.617 mV and 388.534 mV, respectively. This difference ($\Delta E_p$), due to efficient electron transfer, indicated the successful modification of SPCE by chemical immobilization via self-assembled monolayer (SAM) of various components onto the surface of the WE, which at the end of the process, even after several incubation and washing steps, were still stable and active.

Figure 7A:
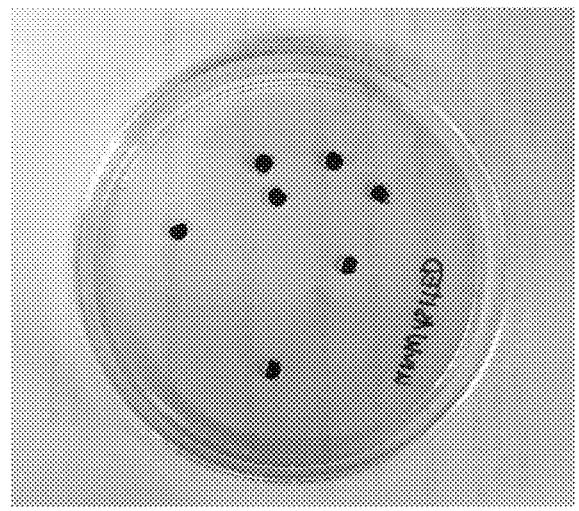
FIG. 7A shows working electrodes (WEs) with immobilized biotinylated O179 bacteriophages on their surfaces.
Figure 7B:
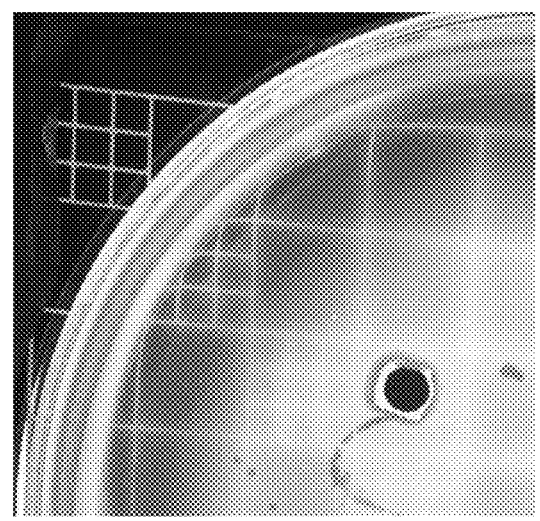
FIG. 7B shows a zone of clearing around one of the WEs from FIG. 7A.

The stability and viability of the immobilized biotinylated bacteriophages (STEC O179) on trimmed WEs of SPCEs were evaluated by conducting agar diffusion method. FIG. 7A shows the WEs themselves, and FIG. 7B shows the results of the agar diffusion test. After a series of washing steps, the result of agar diffusion test showed zones of clearing which were indicative of stable immobilization of the biorecognition elements without negatively affecting their biofunctionality and biocompatibility.

To create the detection element, biotinylated bacteriophages (as previously described) were functionalized with an oxidation catalyst and metal particles. Streptavidin-horseradish peroxidase (S-HRP) (100 μg/mL) (Sigma-Aldrich) and AuNP solution (avg. 13 nm diameter, 20 μM) were both added onto biotinylated bacteriophages (700 μL, >8 log PFU/mL) and incubated overnight at 4° C.

Figure 8:
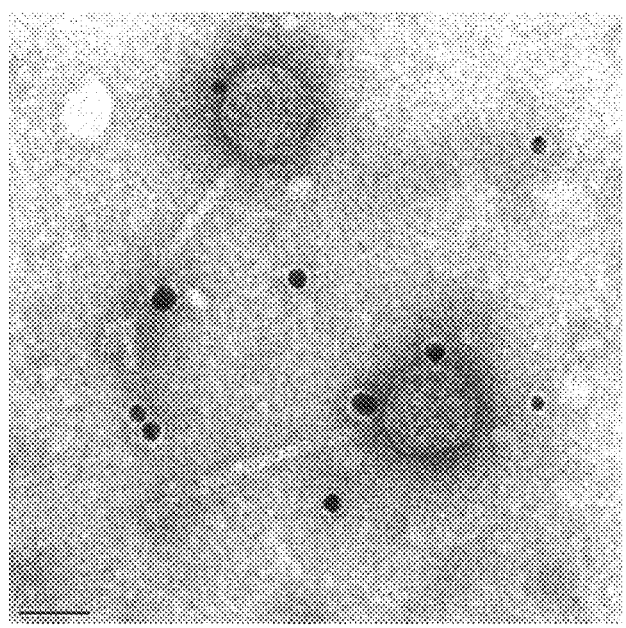
FIG. 8 shows AuNPs, as seen as dark spots, bound to biotinylated STEC O179 bacteriophages. Scale bar: 20 nm.

The viability of the resulting detection element was evaluated using plaque assays with host bacterium and characterized by viewing TEM. In particular, FIG. 8 shows a TEM image of AuNPs bound to the biotinylated bacteriophages (STEC O179).

Testing of the complete device, including the capture element and the detection element, was done with an amperometric device (PalmSense3) as the signal detection device and a phone (Android operating system with the PSTrace5 app installed) as the control device.

Prior to testing the completed device, initial tests were conducted to determine a background noise level of response current (RC) (data not shown). Based on these findings, the assigned baseline RC value was determined to be 900 μA and this level was then subsequently used in all amperometric applications herein.

To conduct the testing, samples (50 μL) including controls were individually dropped onto each working electrode (WE) of biofunctionalized SPCEs and incubated for 12 min at room temperature before washing with 0.5×PBS (100 μL). Once the target STEC cells were captured by the immobilized biotinylated bacteriophages, the detection element (20 μL) was added for sandwich-type detection and incubated at room temperature for 10 min before washing twice with 100 μL volume of TBS-T20 and 0.5×PBS. The mediator (5 μL, 250 mM FeDC in DMSO) was also added. After 30 sec of incubation, 15 μL of hydrogen peroxide (40 mM $H_2O_2$) was also dropped onto the WE. It was allowed to stand for another 30 sec prior to initiating amperometric tests. Amperometric detection was performed with a fixed potential of 0.5 V in all samples (done in triplicates) throughout the trials, 0.5 sec interval within 100 sec run time and an operating temperature around 25° C. (room temp).

The amperometric tests measured the return current and calculated the Δ current, which was then used to determine the specificity and sensitivity of the assay. The signal threshold for positive detection was defined by the signal-to-noise ratio (S/N) as S/N>2, where the target could provide a signal a least three times greater than the signal from non-targets. A linear calibration curve (y=mx+b) assumed the response is linearly related to the concentration, as is known in the art (Shrivastava and Gupta, Methods for the determination of limit of detection and limit of quantitation of the analytical methods, Chron. Young Scientists, 2, 2011; Tolba, et al. A bacteriophage endolysin-based electrochemical impedance biosensor for the rapid detection of Listeria cells, Analyst, 137, 5749, 2012). The limit of detection (LOD) was determined by the statistical significance of signals (Δ current) between non-target bacteria and the lowest inoculum of target bacteria which had a calculated Δ current above signal threshold for positive detection. Fisher's least significant difference (LSD) was used for post-hoc analysis to confirm the significant differences between groups at P<0.05 level.

Specificity and sensitivity testing was done with STEC O26, O179, and O157. Specific biosensors for each strain were prepared and tested. The results of each are shown in Tables 3-5.

TABLE 3

Specificity and sensitivity testing for STEC O26

Specificity

| Bacteria | Log CFU/mL | Δ Current (μA) |
|---|---|---|
| L. monocytogenes | 8 | 27.58 ± 22.54$^a$ |
| S. Typhimurium | 8 | 56.97 ± 38.28$^a$ |
| STEC O26 (target) | 8 | 245.93 ± 44.64$^b$ |

Sensitivity

| Bacteria | Log CFU/mL | Δ Current (μA) | LOD | Coefficient of determination ($R^2$) for linear regression |
|---|---|---|---|---|
| S. Typhimurium | 8 | 15.70 ± 36.03$^a$ | N/A | N/A |
| STEC O26 (target) | 1 | 98.31 ± 26.02$^{ab}$ | 2 log | 0.99 |
| STEC O26 (target) | 2 | 168.25 ± 43.26$^{bc}$ | CFU/ | |
| STEC O26 (target) | 3 | 250.58 ± 43.63$^c$ | mL | |

$^{a,b,c}$Samples with different letters in each section are significantly different (P < 0.05)

TABLE 4

Specificity and sensitivity testing for STEC O179

Specificity

| Bacteria | Log CFU/mL | Δ Current (μA) |
|---|---|---|
| S. Typhimurium | 8 | 57.46 ± 31.6$^a$ |
| STEC O179 (target) | 8 | 172 ± 28.0$^b$ |

Sensitivity

| Bacteria | Log CFU/mL | Δ Current (μA) | LOD | Coefficient of determination ($R^2$) for linear regression |
|---|---|---|---|---|
| S. Typhimurium | 8 | 15.21 ± 11.9$^a$ | N/A | N/A |
| STEC O179 (target) | 1 | 81.19 ± 20.79$^{ab}$ | 2 log | 0.87 |
| STEC O179 (target) | 2 | 141.58 ± 43.32$^b$ | CFU/ | |
| STEC O179 (target) | 3 | 154.17 ± 38.31$^b$ | mL | |

$^{a,b}$Samples with different letters in each section are significantly different (P < 0.05)

TABLE 5

Specificity and sensitivity testing for STEC O157

Specificity

| Bacteria | Log CFU/mL | Δ Current (μA) |
|---|---|---|
| S. Typhimurium | 8 | 8.44 ± 4.0$^a$ |
| STEC O157 (target) | 8 | 126 ± 5.6$^b$ |

Sensitivity

| Bacteria | Log CFU/mL | Δ Current (μA) | LOD | Coefficient of determination ($R^2$) for linear regression |
|---|---|---|---|---|
| S. Typhimurium | 8 | 40.71 ± 23.5$^a$ | N/A | N/A |
| STEC O157 (target) | 1 | 90.09 ± 13.34$^b$ | 1 log | 0.97 |
| STEC O157 (target) | 2 | 124.84 ± 7.35$^{bc}$ | CFU/ | |
| STEC O157 (target) | 3 | 144.08 ± 26.9$^c$ | mL | |

$^{a,b,c}$Samples with different letters in each section are significantly different (P < 0.05)

As can be seen, the biosensor could be adjusted to have high specificity for all tested strains, and a reliable linear regression curve was calculated so that amounts of a target strain could be quantified in a sample solution.

Example 3

Testing in Complex Matrices

Biosensors developed as described above were also tested against complex matrices, specifically food samples. Bacteriophages O26 (STEC host O26:H11 HH8), O157 (STEC host O157:H7 ATCC 35150), and O179 (STEC host O179), also referred to as B-O26, B-O157, and B-O179, respectively, were used for this experiment.

To prepare the food-based matrices, fresh ground beef and pasteurized apple juice were purchased from a local retailer. Weighed fresh ground beef samples (25 g) were transferred into individual stomacher bags (Fisher Scientific). Washed overnight cultures of STEC O26:H11 HH8, O157:H7 ATCC 35150, O179, and *Salmonella* Typhimurium ATCC 14028 in 1×PBS were individually spiked onto the food samples before adding 225 mL of 1×PBS buffered peptone water (BPW) (Thermofisher Scientific) to reach final inoculum levels. Inoculated fresh ground beef samples were then homogenized (10 sec) before taking 50 μL of each sample for amperometric bio sensing. For pasteurized apple juice, 1 mL of the inoculum was added onto 9 mL aliquoted samples and then diluted to reach the same inoculum levels as the fresh ground beef samples. For both food samples, 1×PBS was used to inoculate the control while S. Typhimurium was used for non-target samples. All artificially inoculated food samples were temporarily stored at 4° C. until further use. Two sets of parallel tests were also conducted for verification: conventional PCR targeting stx genes and plate count method using the appropriate selective agar as mentioned in the previous section. Unlike the common traditional methods, this technology did not require pre-enrichment of samples prior to its testing in micro volumes (50 μL).

To test the samples, 50 μL of inoculated (target and non-target) samples were dropped on the WEs of the biosensors. The rest of the method of incubating and washing was identical to that as described above.

The results of each test are shown in Tables 6-8 (ground beef samples) and Table 9-11 (apple juice samples) below.

TABLE 6

Testing for STEC O26 in ground beef

Sensitivity

| Bacteria | Log CFU/mL | Δ Current (μA) | LOD | Coefficient of determination ($R^2$) for linear regression |
|---|---|---|---|---|
| S. Typhimurium | 8 | 41.91 ± 8.13$^a$ | N/A | N/A |
| STEC O26 (target) | 1 | 133.98 ± 23.54$^{ab}$ | 2 log | 0.95 |
| STEC O26 (target) | 2 | 151.71 ± 56.51$^{bc}$ | CFU/ | |
| STEC O26 (target) | 3 | 234.05 ± 65.07$^{cd}$ | mL | |
| STEC O26 (target) | 4 | 295.95 ± 70.32$^d$ | | |

$^{a,b,c,d}$samples with different letters in each section are significantly different (P < 0.05)

TABLE 7

Testing for STEC O157 in ground beef

Sensitivity

| Bacteria | Log CFU/mL | Δ Current (μA) | LOD | Coefficient of determination ($R^2$) for linear regression |
|---|---|---|---|---|
| S. Typhimurium | 8 | 17.33 ± 5.98$^a$ | N/A | N/A |
| STEC O157 (target) | 1 | 39.80 ± 25.43$^b$ | 1 log | 0.98 |
| STEC O157 (target) | 2 | 86.47 ± 54.38$^{bc}$ | CFU/ | |
| STEC O157 (target) | 3 | 112.75 ± 43.79$^c$ | mL | |
| STEC O157 (target) | 4 | 169.57 ± 23.80$^c$ | | |

$^{a,b,c}$Samples with different letters in each section are significantly different ($P < 0.05$)

TABLE 8

Testing for STEC O179 in ground beef

Sensitivity

| Bacteria | Log CFU/mL | Δ Current (μA) | LOD | Coefficient of determination ($R^2$) for linear regression |
|---|---|---|---|---|
| S. Typhimurium | 8 | 33.15 ± 15.75$^a$ | N/A | N/A |
| STEC O179 (target) | 1 | 96.39 ± 57.24$^{ab}$ | 2 log | 0.76 |
| STEC O179 (target) | 2 | 105.81 ± 19.04$^b$ | CFU/ | |
| STEC O179 (target) | 3 | 121.62 ± 44.35$^b$ | mL | |
| STEC O179 (target) | 4 | 222.48 ± 18.92$^c$ | | |

$^{a,b,c}$Samples with different letters in each section are significantly different ($P < 0.05$)

TABLE 9

Testing for STEC O26 in apple juice

Sensitivity

| Bacteria | Log CFU/mL | Δ Current (μA) | LOD | Coefficient of determination ($R^2$) for linear regression |
|---|---|---|---|---|
| S. Typhimurium | 8 | 19.10 ± 8.50$^a$ | N/A | N/A |
| STEC O26 (target) | 1 | 11.15 ± 6.69$^{ab}$ | 2 log | 0.95 |
| STEC O26 (target) | 2 | 97.37 ± 26.96$^{bc}$ | CFU/ | |
| STEC O26 (target) | 3 | 163.14 ± 80.25$^{cd}$ | mL | |
| STEC O26 (target) | 4 | 241.42 ± 45.63$^d$ | | |

$^{a,b,c,d}$Samples with different letters in each section are significantly different ($P < 0.05$)

TABLE 10

Testing for STEC O157 in apple juice

Sensitivity

| Bacteria | Log CFU/mL | Δ Current (μA) | LOD | Coefficient of determination ($R^2$) for linear regression |
|---|---|---|---|---|
| S. Typhimurium | 8 | 39.66 ± 11$^a$ | N/A | N/A |
| STEC O157 (target) | 1 | 125.06 ± 40$^b$ | 1 log | 0 94 |
| STEC O157 (target) | 2 | 178.85 ± 43$^{bc}$ | CFU/ | |
| STEC O157 (target) | 3 | 222.29 ± 41$^c$ | mL | |
| STEC O157 (target) | 4 | 235.16 ± 26$^c$ | | |

$^{a,b,c}$Samples with different letters in each section are significantly different ($P < 0.05$)

TABLE 11

Testing for STEC O179 in apple juice

Sensitivity

| Bacteria | Log CFU/mL | Δ Current (μA) | LOD | Coefficient of determination ($R^2$) for linear regression |
|---|---|---|---|---|
| S. Typhimurium | 8 | 61.36 ± 19.41$^a$ | N/A | N/A |
| STEC O179 (target) | 1 | 171.93 ± 65.34$^{ab}$ | 2 log | 0.83 |
| STEC O179 (target) | 2 | 225.66 ± 24.95$^b$ | CFU/ | |
| STEC O179 (target) | 3 | 245.48 ± 37.38$^b$ | mL | |
| STEC O179 (target) | 4 | 440.51 ± 120.14$^c$ | | |

$^{a,b,c}$Samples with different letters in each section are significantly different ($P < 0.05$)

As can be seen, the bio sensor functions well in complex matrices with reliable linear regression curves so that amounts of a target strain can be quantified in a sample solution.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A biosensor, comprising:
    a capture element comprising a substrate, a surface of the substrate being functionalized with at least one capturing bacteriophage; and
    a detection element comprising at least one detection bacteriophage conjugated to a signal amplification element,
    wherein the capturing bacteriophage and the detection bacteriophage are configured to bind to the same strain or species of a target bacterium, and
    wherein the substrate is one of a printed electrode, a printed circuit board, a silicon-based board, a carbon-based board, or a glass substrate with metal interdigitated electrodes.

2. The biosensor of claim 1,
    wherein the capturing bacteriophage is functionalized with a first conjugating element, and wherein the detection bacteriophage is functionalized with a second conjugating element.

3. The biosensor of claim 2,
wherein the first conjugating element is one of biotin, histadine-tagged nitriloacetic acid, or dithiobis succinimidyl propionate, and
wherein the second conjugating element is one of biotin, histadine-tagged nitriloacetic acid, or dithiobis succinimidyl propionate.

4. The biosensor of claim 1, wherein the capture element further comprises a linking molecule disposed to affix the capturing bacteriophage to the substrate.

5. The biosensor of claim 4, wherein the linking molecule is one of streptavidin or ethanolamine.

6. The biosensor of claim 1, wherein the signal amplification element comprises a particle, the particle being one of a metal particle, a metal oxide particle, or a semiconductor particle.

7. The biosensor of claim 1, wherein the signal amplification element comprises a catalyst.

8. The biosensor of claim 7, wherein the catalyst is one of horseradish peroxidase, soybean peroxidase, glucose oxidase, acetyl cholinesterase, or galactose oxidase.

9. The biosensor of claim 1, further comprising a signal detection device communicatively connected to the capture element.

10. The biosensor of claim 1, wherein the target bacterium is one of *E. coli, Listeria monocytogenes, Campylobacter* spp., and *Staphylococcus* spp.

11. The biosensor of claim 1, wherein the biosensor is configured to be operable using direct sensing of the target bacterium.

12. A kit for the detection of a target bacterium, the kit comprising:
a capture element comprising a substrate, a surface of the substrate being functionalized with at least one capturing bacteriophage;
a detection element comprising at least one detection bacteriophage conjugated to a signal amplification element; and
a signal detection device communicatively connected to the capture element,
wherein the capturing bacteriophage and the detection bacteriophage are configured to bind to the target bacterium.

13. The kit of claim 12, wherein the signal amplification element comprises a particle and a catalyst, the particle being one of a metal particle, a metal oxide particle, or a semiconductor particle.

14. The kit of claim 12, wherein the target bacterium is one of *E. coli, Listeria monocytogenes, Campylobacter* spp., and *Staphylococcus* spp.

15. The kit of claim 12, wherein the kit is configured to be operable using direct sensing of the target bacterium.

16. A method of detecting a target bacterium in a sample, the method comprising:
performing a capture incubation step, the step comprising introducing a capture element to the sample and incubating for a pre-determined capture time;
following the capture incubation step, performing a sandwich incubation step, the step comprising introducing a detection element to the capture element and incubating for a pre-determined sandwich time; and
following the sandwich incubation step, generating a signal to detect the target bacterium,
wherein the capture element comprises a substrate and a capturing bacteriophage functionalized thereon, and
wherein the detection element comprises a detection bacteriophage conjugated to a signal amplification element.

17. The method of claim 16, wherein the pre-determined capture time is between 8-16 minutes.

18. The method of claim 16, wherein the pre-determined sandwich time is between 6-14 minutes.

19. The method of claim 16, further comprising introducing hydrogen peroxide.

20. The method of claim 16, wherein the sandwich incubation step generates a sandwich complex, the sandwich complex comprising the target bacterium disposed between the capture element and the detection element.

21. The method of claim 16, further comprising introducing a mediator.

* * * * *